(12) United States Patent
Johnson et al.

(10) Patent No.: US 10,688,162 B2
(45) Date of Patent: Jun. 23, 2020

(54) HYBRID NEUROTOXINS AND USES THEREOF

(71) Applicant: CellSNAP LLC, Madison, WI (US)

(72) Inventors: Eric A. Johnson, Madison, WI (US); Sabine Pellett, Madison, WI (US); William H. Tepp, Madison, WI (US); Marite Bradshaw, Madison, WI (US); Christina L. Pier, Madison, WI (US); Joseph T. Barbieri, Madison, WI (US)

(73) Assignee: CELLSNAP LLC, Madison, WI (US)

( * ) Notice: Subject to any disclaimer, the term of this patent is extended or adjusted under 35 U.S.C. 154(b) by 0 days.

(21) Appl. No.: 15/866,895

(22) Filed: Jan. 10, 2018

(65) Prior Publication Data

US 2018/0193435 A1 Jul. 12, 2018

Related U.S. Application Data

(60) Provisional application No. 62/444,480, filed on Jan. 10, 2017.

(51) Int. Cl.
*A61K 38/48* (2006.01)
*C07K 14/33* (2006.01)
*C12N 9/52* (2006.01)

(52) U.S. Cl.
CPC .......... *A61K 38/4893* (2013.01); *C07K 14/33* (2013.01); *C12N 9/52* (2013.01); *C12Y 304/24069* (2013.01); *Y02A 50/469* (2018.01); *Y02A 50/473* (2018.01)

(58) Field of Classification Search
None
See application file for complete search history.

(56) References Cited

U.S. PATENT DOCUMENTS

| | | | | | |
|---|---|---|---|---|---|
| 5,939,070 | A * | 8/1999 | Johnson | ................ | C07K 14/33 424/194.1 |
| 6,444,209 | B1 * | 9/2002 | Johnson | ................ | C07K 14/33 424/194.1 |
| 6,545,126 | B1 * | 4/2003 | Johnson | ................ | C07K 14/33 424/94.6 |
| 7,465,457 | B2 * | 12/2008 | Johnson | ................ | C07K 14/33 424/190.1 |
| 7,833,524 | B2 * | 11/2010 | Johnson | ................ | C07K 14/33 424/94.67 |
| 8,440,204 | B2 * | 5/2013 | Johnson | ................ | A61K 39/08 424/239.1 |
| 8,940,477 | B2 * | 1/2015 | Johnson | ................ | C12Q 1/37 435/4 |
| 9,447,405 | B2 * | 9/2016 | Johnson | ................ | C12N 9/96 |
| 10,011,823 | B2 * | 7/2018 | Barbieri | ................ | C12N 9/52 |
| 10,022,450 | B2 * | 7/2018 | Johnson | ................ | C12N 9/96 |
| 2011/0171226 | A1 * | 7/2011 | Johnson | ................ | A61K 39/08 424/140.1 |
| 2014/0255376 | A1 * | 9/2014 | Johnson | ................ | C12N 9/96 424/94.3 |
| 2016/0361429 | A1 * | 12/2016 | Johnson | ................ | C12N 9/96 |
| 2016/0362671 | A1 * | 12/2016 | Johnson | ................ | C07K 14/33 |
| 2018/0117129 | A1 * | 5/2018 | Johnson | ............ | A61K 38/4893 |
| 2018/0161407 | A1 * | 6/2018 | Borodic | ............ | A61K 38/4893 |
| 2018/0193435 | A1 * | 7/2018 | Johnson | ......... | C12Y 304/24069 |

FOREIGN PATENT DOCUMENTS

| | | | | |
|---|---|---|---|---|
| WO | 2015/132004 | | 9/2015 | |
| WO | WO-2018060351 | A1 * | 4/2018 | ............ C07K 14/33 |
| WO | WO-2018107005 | A1 * | 6/2018 | ........... A61K 38/179 |
| WO | WO-2018132423 | A1 * | 7/2018 | ..... C12Y 304/24069 |

OTHER PUBLICATIONS

Pellett et al, Toxicon, 2015, 107:37-42. Available online Jun. 27, 2015 (Year: 2015).*
Marshall et al, BBRC, 2007, 361:49-54. Available online Jul. 20, 2007 (Year: 2007).*
Whitemarsh et al, PLoSONE. Feb. 2014, 9/2:e90252. 6 pages. Published Feb. 27, 2014. (Year: 2014).*
Peck et al, Toxins,2017, 9,38. 21 pages, Published Jan. 18, 2017 (Year: 2017).*
Pellett et al, mBio,9/2:e00089-Mar. 18/Apr. 2018, Published Mar. 27, 2018 (Year: 2018).*
Tepp et al, Applied and Environmental Microbiology, May 2012, 78/9:3108-3113. Published ahead of print: Feb. 24, 2012 (Year: 2012).*
Whitemarsh et al, Infection and Immunity, Oct. 2013, 81/10:3894-3902 Published ahead of print: Aug. 5, 2013 (Year: 2013).*
International Search Report & Written Opinion, International Patent Application No. PCT/US2018/013091, dated Mar. 30, 2018.
Tepp et al. Purification and Characterization of a Novel Subtype A3 Botulinum Neurotoxin; Applied and Environmental Microbiology (May 2012) vol. 78, No. 9 pp. 3108-3113; p. 3108 col. 2, para 3, p. 3112, col. 1, para 2.
Pier et al. Botulinum neurotoxin subtype A2 enters neuronal cells faster than subtype A1 FEBS Letters (Jan. 3, 2011) vol. 585, No. 1, pp. 199-206, abstract, Fig. 5.

* cited by examiner

*Primary Examiner* — Nita M. Minnifield
(74) *Attorney, Agent, or Firm* — Casimir Jones, S.C.

(57) ABSTRACT

The present disclosure relates to chimeric neurotoxins and uses thereof. In particular, provided herein are chimeric botulinum neurotoxins with altered properties and uses thereof (e.g., research, screening, and therapeutic uses).

12 Claims, 8 Drawing Sheets

FIG. 1

| BoNT | Specific toxicity by mouse bioassay |
|------|-------------------------------------|
| rA1A2 | ~1.4 x $10^8$ $LD_{50}$/mg |
| rA2A1 | ~2.5 x $10^8$ $LD_{50}$/mg |
| A2 | ~4 x $10^8$ $LD_{50}$/mg |
| A1 | ~1.2 x $10^8$ $LD_{50}$/mg |

| BoNT | Specific toxicity by mouse bioassay |
|------|-------------------------------------|
| rA1A3 | ~3 x $10^7$ $LD_{50}$/mg |
| rA3A1 | ~8.3 x $10^7$ $LD_{50}$/mg |
| A3 | ~5.9 x $10^7$ $LD_{50}$/mg |
| A1 | ~1.2 $10^8$ $LD_{50}$/mg |

| BoNT | Specific toxicity by mouse bioassay |
|------|-------------------------------------|
| rA4A1 | ~5.6 x $10^7$ $LD_{50}$/mg |
| rA1A4 | ~5.5 x $10^4$ $LD_{50}$/mg |
| rA4 | ~1.1 x $10^5$ $LD_{50}$/mg |
| A1 | ~1.2 x $10^8$ $LD_{50}$/mg |

FIG. 3A

|      | A1A2  | A1    | A2A1  | A2     |
|------|-------|-------|-------|--------|
| EC50 | 2.083 | 3.617 | 1.723 | 0.8410 |

FIG. 3B

|                    | A1A2  | A2A1  | A1    | A2     |
|--------------------|-------|-------|-------|--------|
| EC50               | 2.499 | 9.802 | 2.991 | 13.537 |
| Standard Deviation | 0.158 | 0.280 | 0.505 | 1.777  |

FIG. 4A

HA / Syp1

FIG. 4B

HA :: Syp1

FIG. 4C

Colocalization with Syp1 (n=2)

|      | A1     | A1A3  | A3    | A3A1  |
|------|--------|-------|-------|-------|
| EC50 | 0.3577 | 7.563 | 7.962 | 1.915 |

|  | A1 | A4A1 | A4 | A1A4 |
|---|---|---|---|---|
| EC50 | 0.4402 | 1.848 | 1780 | 1354 |

HYBRID NEUROTOXINS AND USES THEREOF

CROSS REFERENCE TO RELATED APPLICATIONS

This application claims the benefit of U.S. provisional application Ser. No. 62/444,480, filed Jan. 10, 2017, which is incorporated herein by reference in its entirety.

STATEMENT REGARDING FEDERALLY-SPONSORED RESEARCH

This application was supported by Grant No. RO1A1095274 awarded by the National Institutes of Health. The government has certain rights in the invention.

FIELD OF THE DISCLOSURE

The present disclosure relates to hybrid neurotoxins and uses thereof. In particular, provided herein are chimeric botulinum neurotoxins with altered properties and uses thereof (e.g., research, screening, and therapeutic uses).

BACKGROUND OF THE DISCLOSURE

Botulinum neurotoxins (BoNTs), synthesized by the Gram-positive, soil-dwelling bacterium *Clostridium botulinum*, are the most toxic substances known to humankind and are the causative agents of the neuroparalytic disease botulism (Johnson E (2005) in *Topley and Wilson's microbiology and microbial infections*, ed S. P. Borriello, P. R. Murray, and G. Funke (Hodder Arnold, London, United Kingdom), pp 1035-1088). Seven immunologically distinct serotypes of BoNTs designated A through G have been described (Gimenez D F & Gimenez J A (1995) *Int J Food Microbiol* 27: 1-9). BoNTs are initially synthesized as a single-chain polypeptide of ~150 kDa, but posttranslational proteolytic cleavage yields distinct heavy and light chains (HC and LC) of ~100 kDa and ~50 kDa linked by a disulfide bond. The HC is further functionally divided into the $HC_C$ and $HC_N$ sub-domains. The $HC_C$ domain is responsible for recognition and binding to specific neuronal cell surface receptors leading to endocytosis, while the $HC_N$ domain is responsible for channel formation in the endocytic vesicle membrane and translocation and internalization of the LC across the endosomal membrane (Montecucco et al., (2004) *Trends Microbiol* 12: 442-446; Fischer A & Montal M (2007) *J Biol Chem* 282: 29604-29611; Fischer A, et al (2009) *Proc Natl Acad Sci USA* 106: 1330-1335). After translocation, the disulfide bond is cleaved, and the LC is released into the cell cytosol and refolded to the active enzyme component as a zinc-dependent endopeptidase (Fischer et al., supra; Fischer A & Montal M (2007) *Proc Natl Acad Sci USA* 104: 10447-10452; Pirazzini, et al., *Cell Rep* 2014, 8, 1870-1878). The LC then specifically targets and cleaves an intracellular SNARE protein at the pre-synaptic vesicles, which leads to inhibition of neurotransmitter release. Each BoNT serotype has a distinct cleavage target, with BoNT/A and E cleaving SNAP-25 at distinct sites, BoNT/B, D, F, and G cleaving VAMP/synaptobrevin at different sites, and BoNT/C cleaving both SNAP-25 and syntaxin (reviewed in Montecucco C & Schiavo G (1994) *Mol Microbiol* 13: 1-8).

BoNT/A and to a much lesser extent BoNT/B are used as unique and important pharmaceuticals to treat a variety of neuromuscular disorders and in cosmetics. Conditions for which the Food and Drug Administration approved the use of BoNTs include cosmetic treatments and to temporarily relieve a variety of muscle spasticity disorders, hyperhydrosis and migraines (Chaddock J A & Acharya K R (2011) *FEBS J* 278: 899-904). Cosmetic and clinical applications of BoNTs are increasing, and new formulations of BoNTs for pharmaceutical purposes are being developed necessitating clinical trials, accurate potency determination, and neutralizing antibody screening. For example, BoNTs are pharmaceutically administered for the treatment of pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

BoNT with optimized properties for the particular condition being treated or other usage are needed.

SUMMARY OF THE DISCLOSURE

The present disclosure relates to hybrid neurotoxins and uses thereof. In particular, provided herein are chimeric botulinum neurotoxins with altered properties (e.g., activity, duration of activity, etc.) and uses thereof (e.g., research, screening, and therapeutic uses).

For example, in some embodiments, the present disclosure provides a hybrid botulinum neurotoxin (BoNT) toxin molecule comprising at least a portion of a light chain polypeptide from a first subtype and at least a portion of a heavy chain polypeptide from a second subtype. In some embodiments, the BoNT molecule has the same subtype for the heavy and light chain and a portion of the heavy or light chain is exchanged with a portion of a heavy or light chain from a different subtype (e.g., function portion such as a receptor binding domain or translocation domain or catalytic region). In some embodiments, the subtypes are A1, A2, A3, A4, A5, A6, A7, A8, A9, A10, or other subtype. In some embodiments, the molecule has a subtype selected from, for example, A1/A2, A1/A3, A1/A4, A1/A5, A1/A6, A1/A7, A1/A8, A1/A9, A1/A10, A2/A1, A2/A3, A2/A4, A2/A5, A2/A6, A2/A7, A2/A8, A2/A9, A2/A10, A3/A1, A3/A2, A3/A4, A3/A5, A3/A6, A3/A7, A3/A8, A3/A9, A3/A10, A4/A1, A4/A2, A4/A3, A4/A5, A4/A6, A4/A7, A4/A8, A4/A9, A4/A10, A5/A1, A5/A2, A5/A3, A5/A4, A5/A6, A5/A7, A5/A8, A5/A9, A5/A10, A6/A1, A6/A2, A6/A3, A6/A4, A6/A5, A6/A7, A6/A8, A6/A9, A6/A10, A7/A1, A7/A2, a7/A3, A7/A4, A7/A5, A7/A6, A7/A8, A7/A9, A7/A10, A8/A1, A8/A2, A8/A3, A8/A4, A8/A5, A8/A6, A8/A7, A8/A9, A8/A10, A9/A1, A9/A2, A9/A3, A9/A4, A9/A5, A9/A6, A9/A7, A9/A8, A9/A10, A10/A1, A10/A2, A10/A3, A10/A4, A10/A5, A10/A6, A10/A7, A10/A8, or A10/A9. In some embodiments, the molecule has a subtype of A1/A3 or A1/A2. In some embodiments, wherein the molecule further comprises one or more amino acid changes that alter a property (e.g., duration, potency, or cell entry and intracellular transport speed). In some embodiments, the molecule exhibits one or more properties selected, for example, from altered duration of action relative to BoNTs having light chains and heavy chains of the same subtype, altered neuronal selectivity relative to BoNTs having light chains and heavy chains of the same subtype, altered potentcy relative to BoNTs having light chains and heavy chains of the same subtype, altere onset of action relative to BoNTs having light chains and heavy chains of the same subtype, or altered distribution characteristics including neuronal cell uptake or transport relative to BoNTs having light chains and heavy chains of the same subtype. In some embodiments, the molecule has a serotype selected from, for example, A, B, C1, D, E, F, or G. In some embodiments, the light chain and said heavy chain have the same or different serotypes.

Further embodiments provide a hybrid botulinum neurotoxin (BoNT) molecule comprising an A1/A3 subtype (e.g., exhibiting longer duration, higher potency, and altered neuronal distribuation relative to BoNTs having light chains and heavy chains of the same subtype).

Additional embodiments provide a hybrid botulinum neurotoxin (BoNT) molecule comprising an A1/A2 subtype (e.g., exhibiting longer duration, higher potency, and faster cell entry and intracellular transport relative to BoNTs having light chains and heavy chains of the same subtype).

Yet other embodiments provide one or more nucleic acids encoding the molecules described herein or a vector comprising the nucleic acid. Some embodiments comprise a cell comprising the vector (e.g., a *Clostridium botulinum* or *E. coli* cell).

Still additional embodiments comprise a composition (e.g., pharmaceutical composition) comprising the molecules. In some embodiments, the composition further comprises a pharmaceutically acceptable carrier.

In some embodiments, the present disclosure provides the molecules described herein for use in medicine (e.g., to treat, prevent, or reduce the severity of signs or symptoms of any of the diseases or conditions described herein).

In other embodiments, the present disclosure provides the use of the molecule or composition described herein for the manufacture of a medicament (e.g., to treat, prevent, or reduce the severity of signs or symptoms of any of the diseases or conditions described herein).

In still further embodiments, the present disclosure provides a method, comprising: administering the the molecules or compositons described herein to a subject in need thereof. In some embodiments, the administration is local or systemic. In some embodiments, the subject is diagnosed with or has symptoms of a disorder or condition selected from, for example, pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, non-achalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, or myelon tumor.

Additional embodiments are described herein.

DESCRIPTION OF THE FIGURES

FIG. 1 shows SDS-PAGE gels of purified 150 kDa chimeric BoNT/A subtypes toxins and specific activity in mice.

FIG. 3A-B shows activity of BoNT/A subtype hybrids in human neurons. A. Activity and entry kinetics of BoNT/A1A2 and A2A1 subtype chimeras in human neurons. B. In Vitro endopeptidase activity of A1A2 and A2A1 hybrids.

FIG. 4A-C shows interaction of BoNT/A subtype hybrids with rat primary neurons. HCR/A1 and HCR/A2 and the HCRA chimeras were assayed for association with primary rat neurons (A) and co-localization with SV2, a marker for synaptic vesicles (B). (C) shows neuronal cell association of non-toxic, non-catalytic full length engineered BoNT variants.

DEFINITIONS

Figure 2:
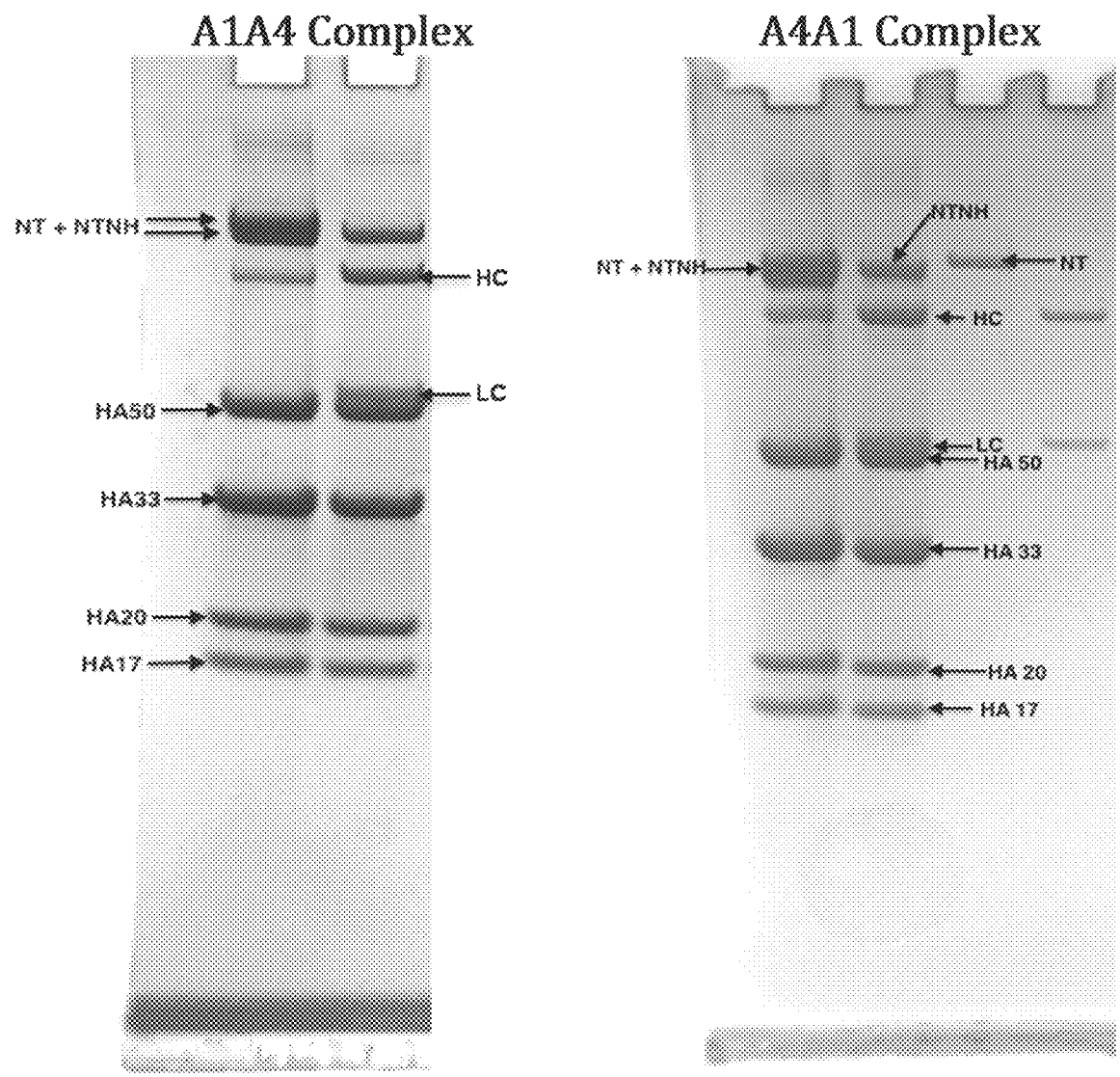
FIG. 2 shows SDS-PAGE gels of purified 150 kDa chimeric BoNT/A1A4 and A4A1 subtypes toxin complex.

To facilitate an understanding of the present disclosure, a number of terms and phrases are defined below:

As used herein, the term "A1/A3" and the like refers to a BoNT molecule with a light chain derived from the A serotype and the 1 subtype and a heavy chain derived from the A serotype and the 3 subtype (A2/A4 having a light chain from the 2 subtype and a heavy change from the 4 subtype; etc.).

As used herein, the term "exhibits one or more altered properties" (e.g., altered duration of action relative to BoNT having light chains and heavy chains of the same subtype, altered neuronal selectivity relative to BoNT having light chains and heavy chains of the same subtype, altered potency relative to BoNT having light chains and heavy chains of the same subtype, altered onset of action relative to BoNT having light chains and heavy chains of the same subtype, or altered uptake or transport relative to BoNT having light chains and heavy chains of the same subtype) refers to a property of a hybrid BoNT (e.g., those described herein) that is altered relative to a BoNT having light chains and heavy chains of the same subtype. In some embodiments, BoNTs having heavy and light chains of the same subtype or hybrid BoNTs have one or more amino acid changes relative to the sequence of the corresponding BoNT found in nature.

As used herein, the term "host cell" refers to any eukaryotic or prokaryotic cell (e.g., bacterial cell, mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos and stem cell derived cells.

As used herein, the term "pharmaceutical composition" refers to the combination of an active agent with a carrier, inert or active, making the composition especially suitable for diagnostic or therapeutic use in vitro, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include cells, tissues, blood products, such as plasma, serum and the like. Such examples are not however to be construed as limiting the sample types applicable to the present disclosure.

DETAILED DESCRIPTION OF THE DISCLOSURE

The present disclosure relates to hybrid neurotoxins and uses thereof. In particular, provided herein are chimeric botulinum neurotoxins with altered properties and uses thereof (e.g., research, screening, and therapeutic uses).

Botulinum Neurotoxins (BoNTs) are the causative agent of botulism and are also widely used as important pharmaceuticals to treat a variety of neurologic diseases. There are seven immunologically distinct serotypes of BoNTs (A-G) that differ in amino acid sequence by 40-70%. Additionally, each of the serotypes has several subtypes that differ in amino acid sequence by 0.9-36%. Approximately 40 different subtypes have been described to date. However, only two subtypes of BoNTs, BoNT/A1 and B1 are currently used as therapeutics. BoNT sero- and subtypes differ in their biological and pharmacological characteristics such as onset and duration of action, neuronal selectivity, and potency. BoNT/A1 is used most commonly in medicine mainly due to the long duration of activity of its light chain (LC) inside the neuronal cell cytosol compared to other serotypes. Purification and analysis of BoNT/A subtypes (A1-A5) during the development of embodiments of the present disclosure has indicated distinct potency, duration of action, neuronal selectivity, and unique pharmacological activities within the subtypes.

Accordingly, provided herein are hybrid, recombinant BoNTs comprising the LC of one BoNT subtype and the heavy chain (HC) of another BoNT subtype. In experiments conducted during the course of development of embodiments of the present disclosure, the hybrid toxins were produced in an endogenous (*Clostridium botulinum*) expression host without use of additional methods such as linkers between the LC and HC or tags for purification (Table 1). The 150 kDa toxins were purified and specific activity determined by mouse bioassay (FIG. 1). Analysis of the hybrids indicate that they purify as toxin complexes (FIG. 2), similar to the native BoNTs, and that they are properly processed in the expression host leading to the dichain BoNT consisting of the LC and HC linked via a disulfide bond (FIGS. 1 and 2). Specific toxicity in mice is similar to that of native BoNT/A subtypes (FIG. 1), and neuronal cell-based assays and in vitro endopeptidase assays have indicated consistency of enzymatic activity and duration of actions by the LCs but distinct uptake characteristics of the chimeras (FIG. 3). An *E. coli* expression system for expression of BoNTs is also provided herein.

Such hybrid BoNTs comprising or consisting of domains of different subtypes or serotypes and expressed in their native and fully functional form or in heterologous hosts such as *E. coli* provide new therapeutic compositions with unique characteristics and desired pharmacological properties. In addition, this technology offers a platform for construction of therapeutics that are selected to contain specific desired characteristics such as a specified duration of action, in vivo distribution, and immunological distinction from currently used BoNT based pharmaceuticals. In some exemplary embodiments, BoNT/A1A3 (A1 LC with long duration and high potency and A3 HC with unique distribution) and BoNT/A1A2 (A1 LC with long duration and high potency and A2 HC with faster cell entry and intracellular transport characteristics) are exemplified as therapeutics for use in humans. These hybrid toxins offer different treatment modalities (BoNT/A1A3) and greater safety and potency due to faster cell entry and less spread from the injection site (BoNT/A1A2), and are alternatives for treatments of patients that have developed antibodies to BoNT/A1. In particular, BoNT/A1A2 evades neutralization by an existing immune response, as it enters the neurons more rapidly.

Exemplary construct BoNT/A1A3 (A1 LC with long duration and high potency and A3 HC with unique distribution) and BoNT/A1A2 (A1 LC with long duration and high potency and A2 HC with faster cell entry and intracellular transport characteristics) provide enhanced therapeutics for use in humans. Such hybrid BoNTs have the following advantages over the currently used BoNT/A1: BoNT/A1A3 offers different treatment modalities due to its unique distribution in vivo, while maintaining the long duration of BoNT/A1. BoNT/A1A2 offers greater safety and potency due to faster cell entry and less spread from the injection site while maintaining the long duration of BoNT/A1. Both hybrids provide alternatives for treatments of patients that have developed antibodies to BoNT/A1. In particular, it is contemplated that BoNT/A1A2 evades neutralization by an existing immune response, as it enters the neurons more rapidly.

The molecular mechanism underlying the long duration of BoNTs is currently one of the largest unsolved questions in BoNT research. While desirable for therapeutic purposes, the long duration of action of BoNTs after neuronal cell entry, when the toxins are not accessible to antitoxin treatments, is largely responsible for the severity of botulism pathology. The BoNT/A3 subtype variant of BoNT/A has a significantly shorter duration of action compared to BoNT/A1, 2, 4, and 5 (Pellett et al., Toxicon. 2015; 107(Pt A):37-42. Epub 2015 Jul. 2; Whitemarsh et al., PLoS One. 2014; 9(2):e90252. Epub 2014 Mar. 4). Some pharmaceutical applications may desire a shorter duration of action, and the A3A1 chimera provides a pharmaceutical of shorter duration and similar distribution, potency, and cell entry characteristics as A1.

In some embodiments, the BoNT subtypes are one of the following accession numbers or polypeptides with at least 80% (e.g., 80%, 85%, 90%, 91%, 92%, 93%, 94%, 95%, 96%, 97%, 98%, 995, or 100%) identify to such polypeptides:

A1: AF461540
A2: X73423
A3: EU341306
A4: EU341306
A5: HM153705.1

In some embodiments, BoNT molecules are modified to enhance or alter one or more properties (e.g., cell entry or duration of action) by introduction of specific structural elements or amino acids. In some embodiments, the region of the BoNT responsible for a specific property is altered, leaving the rest of the molecule (and other properties) unchanged.

In some embodiments, the BoNT molecule has the same subtype for the heavy and light chain and a portion of the heavy or light chain is exchanged with a portion of a heavy or light chain from a different subtype (e.g., function portion such as a receptor binding domain or translocation domain or catalytic region).

The below Table 1 shows exemplary combinations of BoNT heavy and light chains.

TABLE 1

| Light Chain | Heavy Chain |
|---|---|
| A1 | A2 |
| A1 | A3 |
| A1 | A4 |
| A1 | A5 |
| A1 | A6 |
| A1 | A7 |
| A1 | A8 |
| A1 | A9 |

TABLE 1-continued

| Light Chain | Heavy Chain |
|---|---|
| A1 | A10 |
| A2 | A1 |
| A2 | A3 |
| A2 | A4 |
| A2 | A5 |
| A2 | A6 |
| A2 | A7 |
| A2 | A8 |
| A2 | A9 |
| A2 | A10 |
| A3 | A1 |
| A3 | A2 |
| A3 | A4 |
| A3 | A5 |
| A3 | A6 |
| A3 | A7 |
| A3 | A8 |
| A3 | A9 |
| A3 | A10 |
| A4 | A1 |
| A4 | A2 |
| A4 | A3 |
| A4 | A5 |
| A4 | A6 |
| A4 | A7 |
| A4 | A8 |
| A4 | A9 |
| A4 | A10 |
| A5 | A1 |
| A5 | A2 |
| A5 | A3 |
| A5 | A4 |
| A5 | A6 |
| A5 | A7 |
| A5 | A8 |
| A5 | A9 |
| A5 | A10 |
| A6 | A1 |
| A6 | A2 |
| A6 | A3 |
| A6 | A4 |
| A6 | A5 |
| A6 | A7 |
| A6 | A8 |
| A6 | A9 |
| A6 | A10 |
| A7 | A1 |
| A7 | A2 |
| A7 | A3 |
| A7 | A4 |
| A7 | A5 |
| A7 | A6 |
| A7 | A8 |
| A7 | A9 |
| A7 | A10 |
| A8 | A1 |
| A8 | A2 |
| A8 | A3 |
| A8 | A4 |
| A8 | A5 |
| A8 | A6 |
| A8 | A7 |
| A8 | A9 |
| A8 | A10 |
| A9 | A1 |
| A9 | A2 |
| A9 | A3 |
| A9 | A4 |
| A9 | A5 |
| A9 | A6 |
| A9 | A7 |
| A9 | A9 |
| A9 | A10 |
| A10 | A1 |
| A10 | A2 |
| A10 | A3 |
| A10 | A4 |
| A10 | A5 |
| A10 | A6 |
| A10 | A7 |
| A10 | A8 |
| A10 | A9 |

While the present disclosure is exemplified with the A serotype of BoNT, the present disclosure is not limited to particular BoNT serotypes. In some embodiments, the molecule has a serotype selected from, for example, A, B, C1, D, E, F, or G and subtypes thereof. In some embodiments, the light chain and said heavy chain (e.g., as described above) have the same or different serotypes. For example, as described above, in some embodiments, both the heavy and light chain are BoNT A serotypes. In some embodiments, the heavy chain is an A serotype (e.g., A1-A10) and the light chain is a B, C1, D, E, F, or G serotype or other combinations thereof. Exemplary serotype combinations include, but are not limited to (light chain:heavy chain) A:A; A:B; A:C1; A:D; A:E; A:F; A:G; B:A; B:B; B:C1; B:D; B:E; B:F; B:G; C1:A; C1:B; C1:C1; C1:D; C1:E; C1:F; C1:G; D:A; D:B; D:C1; D:E; D:F; D:G; E:A; E:B; E:C1; E:D; E:F; E:G; F:A; F:B; F:C1; F:D; D:E; F:F; F:G1 G:A; G:B; G:C1; G:D; G:E; G:F; and G:G. Within these serotypes, any combination of subtypes may be utilized (e.g. including but not limited to, the A serotype combinations described in Table 1, BoNT B1-B7, BoNT C1, BoNT D subtypes, BoNT E1-6, BoNT F1-7, and BoNT G subtypes). In some embodiments, hybrid BoNT molecules are prepared using a manufacturing process described, for example, in Dressler D. HNO. 2012 June; 60(6):496-502; Wortzman M S, Pickett A. Aesthet Surg J. 2009 November; 29(6 Suppl):S34-42; each of which is herein incorporated by reference in its entirety or another suitable method.

In some embodiments, hybrid BoNT molecules are provided as pharmaceutical compositions.

The compounds described herein, optionally together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

BoNT compositions are typically administered via injection, although other delivery methods are specifically contemplated.

The dose, when using the compounds and formulations described herein, can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds. Representative doses include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, for use in treatment will vary with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds described herein and as part of a drug combination. The dosage regimen for treating a disease condition with the compounds and/or compositions is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods described herein.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed, as a solvent or suspending medium. For this purpose any bland fixed oil may be employed including synthetic mono- or diglycerides. In addition, fatty acids such as oleic acid find use in the preparation of injectables.

The compounds according may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

In some embodiments, compositions comprising hybrid BoNT molecules comprise purified BoNT (hybrid) stabilized and preserved, e.g. with human serum albumin and non-protein stabilizers. These may be derived from non-human and non-animal sources. In some embodiments, hybrid BoNT are provided in combination with native complexes. In some embodiments, compositions are in a pH neutral buffer and stabilized with human serum albumin in stabilized liquid formulation. In some embodiments, compositions are lyophilized for re-suspension in saline or sterile water.

The hybrid BoNT preparations described herein find use in the treatment of a variety of conditions including, but not limited to, cosmetic treatments and to temporarily relieve a variety of muscle spasticity disorders, hyperhydrosis and migraines (Chaddock J A & Acharya K R (2011) *FEBS J* 278: 899-904; Dressler, D. Clinical applications of botulinum toxin. In Curr opin microbiol, England, 2012; Vol. 15, pp 325-336; Dressler, D. Botulinum toxin drugs: Brief history and outlook. J Neural Transm (Vienna) 2016, 123, 277-279.). Cosmetic and clinical applications of BoNTs are increasing, and new formulations of BoNTs for pharmaceutical purposes are being developed necessitating clinical trials, accurate potency determination, and neutralizing antibody screening. For example, BoNTs are pharmaceutically administered for the treatment of pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

EXPERIMENTAL

The following examples are provided in order to demonstrate and further illustrate certain preferred embodiments and aspects of the present disclosure and are not to be construed as limiting the scope thereof.

Example 1

Materials and Methods:

Plasmid construction. Individual LC and HC gene regions from BoNT/A1, A2, A3, and A4 botulinum neurotoxin genes were amplified by PCR. An approximately 50 bp region located between the LC and HC is homologous between the toxin genes. Therefore, PCR primers were designed to contain a portion of this region that enabled generation of a seamless junction between the two different subtype gene regions in a hybrid toxin gene using overlap PCR (FIG. 1). The recombinant toxin genes do not contain any additional amino acid residues or protein tags (Table 1). The sequence of all recombinant genes was verified by sequencing.

The recombinant genes were then inserted into clostridial expression vectors, and the expression constructs were transferred by conjugation to the nontoxigenic *C. botulinum* expression host strain Hall A-hyper/tox– from an *E. coli* CA434 donor strain as previously described (Bradshaw et al., Appl Environ Microbiol. 2014; 80(23):7415-22. Epub 2014 Sep. 23). The expression of the hybrid toxins was assessed by Western blots and mouse bioassays. Recombinant hybrid BoNTs were purified following procedures developed for BoNT/A1 (Malizio et al., Methods in molecular biology (Clifton, N.J.). 2000; 145:27-39).

Botulinum Neurotoxins.

BoNT/A1 was purified from *C. botulinum* strains Hall A-hyper from the Johnson laboratory stock and BoNT/A3 from *C. botulinum* CDC A3 (kindly provided by Susan Maslanka and Brian Raphael, Centers for Disease Control and Prevention, Atlanta, Ga.) as previously described (Malizio et al., supra; Tepp et al., Appl Environ Microbiol. 2012; 78(9):3108-13. Epub 2012 Mar. 1). Recombinant BoNT/A1A3 and BoNT/A3A1 were produced in a nontoxigenic strain of *C. botulinum* (Hall A-hyper/tox-) and purified similarly as described (Bradshaw et al., Appl Environ Microbiol. 2014. Epub 2014 Sep. 23). Purity of the toxins was confirmed by spectroscopy and SDS-PAGE analyses. The purified toxins were stored in phosphate buffered saline with 40% glycerol at −20° C. until use.

Cell-Based Toxicity Assay.

Cell based assays were performed essentially as previously described (Whitemarsh et al., Toxicological sciences: an official journal of the Society of Toxicology. 2012; 126(2):426-35). Human induced pluripotent stem cell (hiPSC) derived neurons (iCell Neurons) were purchased from Cellular Dynamics International (CDI, Madison, Wis.) and were seeded into 96-well TPP plates (Techno Plastic Products, Midwest Scientific, Valley Park, Mo.) that had been coated with 0.01% poly-L-ornithine and 8.3 µg/cm2 Matrigel (BD Biosciences, East Rutherford, N.J.) at a density of about 35,000-40,000 cells per well. The cells were maintained in the provided culture media as per company instructions. At 5-7 days post seeding, the cells were used for the toxin activity and neutralization assays. The primary rat spinal cord (RSC) cells were prepared from EIS Sprague Dawley rat pups and seeded into 96-well TPP plates that had been coated with 0.01% poly-L-ornithine and 8.3 µg/cm2 Matrigel at a density of 50,000 cells/well. RSC cells were maintained in Neurobasal media supplemented with B27, glutamax, and penicillin/streptomycin (all from Life Technologies) as previously described (Pellett et al., FEBS letters. 2007; 581(25):4803-8; Pellett et al., Journal of pharmacological and toxicological methods. 2010; 61(3):304-10) and used for the toxin assay after 19 days in culture.

For the toxin activity assay, serial dilutions of purified BoNT were prepared in the respective cell culture medium. The cells were exposed to the serial toxin dilutions in 50 µl of culture media for 48 h at 37° C., 5% $CO_2$. The toxin was aspirated from the cells, and cell lysates were prepared in 50 µl of lithium dodecyl sulfate (LDS) sample buffer (Life Technologies). The cell lysates were analyzed by Western blot for VAMP2 cleavage as previously described (Pellett et al., FEBS letters. 2007; 581(25):4803-8; Pellett et al., Journal of pharmacological and toxicological methods. 2010; 61(3):304-10). Images were obtained using PhosphaGlo reagent (KPL, Gaithersburg, Md.) and a Fotodyne/FOTO/Analyst FX imaging system (Harland, Wis.), and the cleaved and uncleaved SNAP-25 bands were analyzed by densitometry using TotalLab Quant software (Fotodyne, Harland, Wis.). EC50 values were estimated using GraphPad Prism 6 software and a nonlinear regression, variable slope, four parameters.

Mouse Assays.

Activities of the subtype and hybrid toxin preparations were determined using a standard intraperitoneal mouse bioassay (MBA) as previously described (Schantz, Journal of the Association of Official Analytical Chemists. 1978; 61:96-9; Hatheway C L. Botulism. In: Balows A, Hausler W H, Ohashi M, Turano M A, editors. Laboratory diagnosis of infectious diseases: principles and practice. New York: Springer-Verlag; 1988. p. 111-33). The half-lethal dose of each toxin was defined as 1 mouse LD50 Unit (U). In vivo duration of action was determined by DAS (digital abductions core) and Rotarod analysis as previously described (Pellett et al., Toxicon. 2015; 107(Pt A):37-42. Epub 2015 Jul. 2). In short, groups of 5 female ICR mice (Harlan) were injected into the right gastrocnemius muscle with the indicated sub-lethal amounts of toxin in 10 µl of GelPhos buffer (30 mM sodium phosphate [pH 6.3] and 0.2% gelatin) using an insulin syringe. The mice's ability to remain running on a Rotarod (MED-Associates) using an accelerating cycle of 4-40 rpm over 5 min was determined daily until full recovery.

Results:

Hybrid Toxins Combining HC and LC Domains of BoNT/A Subtypes can be Produced in a Clostridial Expression System.

Studies indicated several biological and functional differences between BoNT/A subtypes, including a shorter duration of action of BoNT/A3, faster cell entry and greater potency of /A2, and lower potency of /A4 as well as differential potency of /A3 in human cell models. In order to determine roles of the HC and LC domains in each of these functions, hybrid toxins consisting of the HC domain of /A1 and LC domain of /A2, /A3, or /A4 and the opposite constructs were prepared. In order to avoid potential influences of added structural elements, no tags or linkers were added such that the hybrid toxins contained only the translated bont gene sequences of the HC and LC domains, respectively, joined by their natural disulfide bond. The constructs were expressed in a clostridial expression host derived from strain Hall to enable proper post-translational processing of the toxins. Analysis of the purified toxins indicated pure 150 kDa toxin preparations and proper processing to the dichain form (FIG. 1). Mouse bioassays to determine specific activity indicated that the hybrid toxins containing the /A1 HC all had similar activity to that of BoNT/A1, whereas the hybrid toxins containing the A1 LC were similar in activity to the respective HC parent toxin (FIG. 1). These data indicate that functional hybrid toxins were produced and had undergone proper post-translational processing in a native clostridial expression host, and that potency of the BoNT/A subtypes 1-4 is primarily determined by the HC domain.

The Hybrid Toxins can be Purified as Toxin Complexes.

The hybrid BoNTs were expressed in a clostridial expression system that contains all naturally expressed BoNT/A non-toxic complex proteins (Bradshaw et al., Appl Environ Microbiol. 2014; 80(23):7415-22. Epub 2014 Sep. 23). The toxins were purified using biochemical methods, and SDS-PAGE gel analyses indicated that as part of the purification procedure toxin complexes were purified (FIG. 2). This indicates that engineered BoNT/A subtype hybrid toxins can be produced as the more stable toxin complexes, and confirms proper posttranslational folding and processing of the toxins. The 150 kDa proteins were then purified from the complexes in further purification steps (see FIG. 1).

The Faster Cell Entry Kinetics of BoNT/A2 is Primarily Determined by its HC Domain.

Previous analyses of BoNT/A1 and A2 had indicated that BoNT/A2 is more potent in cultured neurons and has faster cell entry kinetics compared to BoNT/A1. Potency of the BoNT/A1A2 and /A2A1 and their parent toxins was compared in iCell Neurons (hipSC derived neurons) after exposure to serial dilutions for 48 h in parallel. The data showed an intermediate activity of both hybrid toxins to the parent toxins, indicating that the hybrid toxins both had greater potency in cultured neurons compared to BoNT/A1 (FIG. 3A). One of the relevant properties of BoNT/A2 is its faster cell entry as compared to BoNT/A1. Cell entry kinetics studies in hiPSC derived neurons were conducted by exposing the neurons to equal amounts of the toxins, and measuring SNAP-25 cleavage over time. While neither chimera entered neurons as fast as BoNT/A2, the /A1 A2 hybrid, containing the /A2 HC, approached the faster cell entry profile of the A2 parent toxin (FIG. 3A). The /A2A1 hybrid enter cells only slightly faster than the A1 parent toxins. This indicates that the cell entry characteristics of these toxins are localized primarily to the HC of these toxins.

Comparison of the LC activities of the hybrids and parent toxins by an endopeptidase assay showed that the LC activity of BoNT/A1A2 and BoNT/A1 was greater than that of BoNT/A2 and BoNT/A2A1 (FIG. 3B). This is in agreement with data indicating a reduced activity of the BoNT/A2 LC comprising the HC portion of A2 responsible for faster cell entry and the greater enzymatic activity of the A1 LC yields a construct with improved pharmaceutical properties of faster cell entry and even greater potency than BoNT/A2.

The Receptor Binding Properties of BoNT/A2 are Localized to the C-Terminal Subdomain of the HCR.

Previous observations on the association of the BoNT/A1 and A2 HC receptor binding domains (HCR) with neuronal cells have indicated greater association of BoNT/A2 HCR than BoNT/A1 HCR with cultured neurons (Whitemarsh et al., Neuronal Cell Cultures, and In Vitro. Infect Immun. 2013; 81(10):3894-902. Epub 2013 Aug. 7). In order to identify the structural sub-domain responsible for greater cell association, BoNT/A1 and 2-HCR variants were engineered to assess how the subdomains of the receptor binding domains of HCRs contribute to interaction with neurons. HCR domains encode residues 876-1295 of BoNT/A1 and BoNT/A2 with two subdomains: an N-terminal 876-1079 subdomain ($HCR_N$) and a 1080-1295 subdomain ($HCR_C$). HCR/A subdomain chimeras were engineered to determine how each subdomain contributes to entry and intracellular trafficking in neurons, including HCR/A1A2 which encoded [HCRA1(876-1079)-HCRA2(1080-1295)] and HCR/A2A1 which encoded [HCRA1(876-1079)-HCRA2(1080-1295)]. HCR/A1 and HCR/A2 and the HCRA chimeras were assayed for association with primary rat neurons and co-localization with SV2, a marker for synaptic vesicles (FIG. 4).

HCR/A2 had greater association with primary cortical neurons than HCR/A1, while HCRA1A2 associated with primary cortical neurons similar to HCR/A2, and HCR/A2A1 associated with primary cortical neurons similar to HCR/A1 (FIG. 4A). This indicated that receptor binding functions were defined by residues within the C-terminal subdomain (residues 1080-1295) of the HCR. Both HCRA1 and HCR/A2 had a greater association with synaptic vesicles when synaptic vesicle cycling was stimulated than in resting neurons, suggesting that the native HCRs had similar affinities for synaptic vesicles. HCR/A1A2 showed a similar association with synaptic vesicles having a greater association with synaptic vesicles when synaptic vesicle cycling was stimulated than in resting neurons. Unexpectedly, HCR/A2A1 showed a lower association with synaptic vesicles when synaptic vesicle cycling was stimulated or when neurons were in a resting state (FIG. 4B). This indicates that the HCR can be modified to change intracellular trafficking properties and how the protein traffics in neurons.

To analyze cell association of full-length toxin constructs in a safe manner, full-length non-toxic, non-catalytic BoNT variants were engineered. These BoNT variants encode three amino acid mutations (RYE) within the light chain that renders the protein nontoxic in mice. Two BoNT/A variants were engineered and produced in an *E. coli* expression system: BoNT/A1(RYE) and BoNT/A1A2(RYE). BoNTA1A2(RYE) encodes the N-terminal 1-875 for BoNT/A1 and the C-terminal 876-1295 of BoNT/A2. BoNT/A1 (RYE) and BoNTA1A2 HCR/A2 and the HCR/A chimeras were assayed for co-localization with synaptophysin 1 (Syp1), a marker protein for synaptic vesicles. While each of the BoNT variants increased association with synaptic vesicle cycling, BoNT/A1A2 showed greater synaptic vesicle association relative to BoNT/A1. This is consistent with the HCR defining receptor recognition and entry into synaptic vesicles.

BoNT/A2 and the BoNT/A2/A1 variant with subsequent construction of the HCR subdomain variants that were described in FIG. 4 are engineered to further characterize the role of the two HCR subdomains in BoNT entry and trafficking into neurons.

Both the HC and LC Domain of BoNT/A3 Determine its Potency in Human neurons.

Analyses of BoNT/A1 and A3 had indicated that human neurons are over 50-fold less sensitive to BoNT/A3 than to BoNT/A1 when comparing biological activity of the toxins in cultured human neurons. To determine whether the lower sensitivity of human neurons to BoNT/A3 was due to the toxins HC or LC portion, the hybrid toxins were analyzed in the same human neuronal cell model. Human induced pluripotent stem cell (hiPSC) derived neurons (iCell neurons) were exposed to serial dilutions of the hybrid toxins and the parental toxins in parallel. While BoNT/A1 resulted in an activity similar as previously observed (about 0.3 $LD_{50}$ U/well), the activity of BoNT/A3 was about 2-fold higher than previously reported (about 5 $LD_{50}$ U/well), such that the difference in sensitivity between BoNT/A1 and A3 was about 15-fold. Since new toxin stocks were used for this experiment, this can be attributed to stock-specific differences. The sensitivity to both hybrid toxins was between 1 and 2 $LD_{50}$ U/well, falling in between the activities of the parental toxins (FIG. 5 A). These data indicate that potency of BoNT/A3 is determined by both the HC and LC domains of the toxin.

The Duration of Action is Determined Exclusively by the BoNT LC Domain.

Figure 5A:
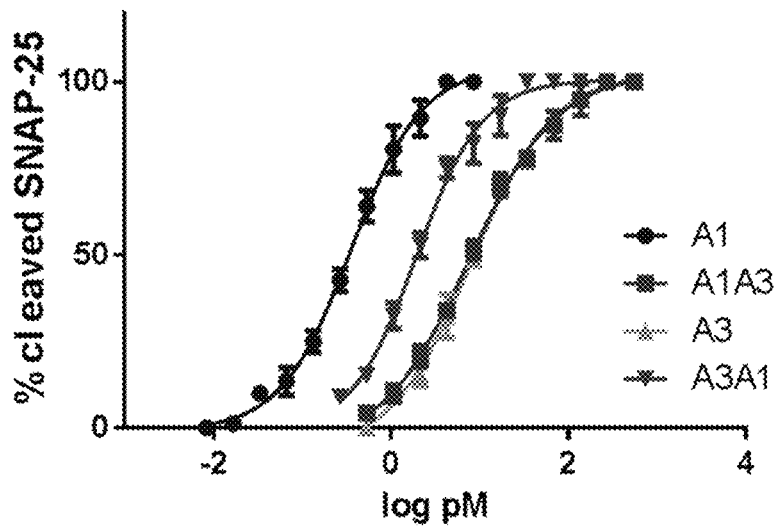
FIG. 5A-C shows duration of action of BoNT/A1A3 and A3A1 chimeras. Duration of action was examined in human neurons (A), in cultured rat spinal cord neurons (B), and in mice in vivo (C).
Figure 5B:
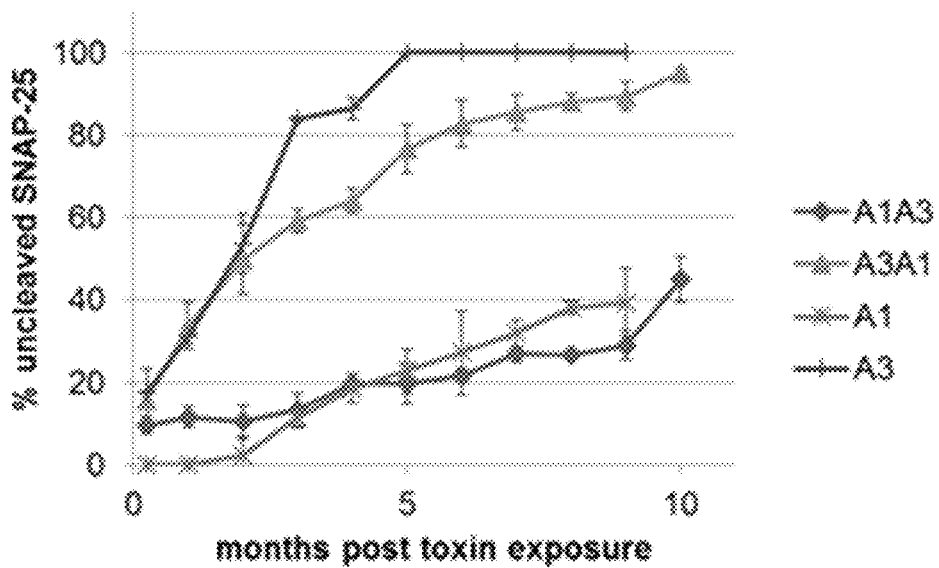
Figure 5C:
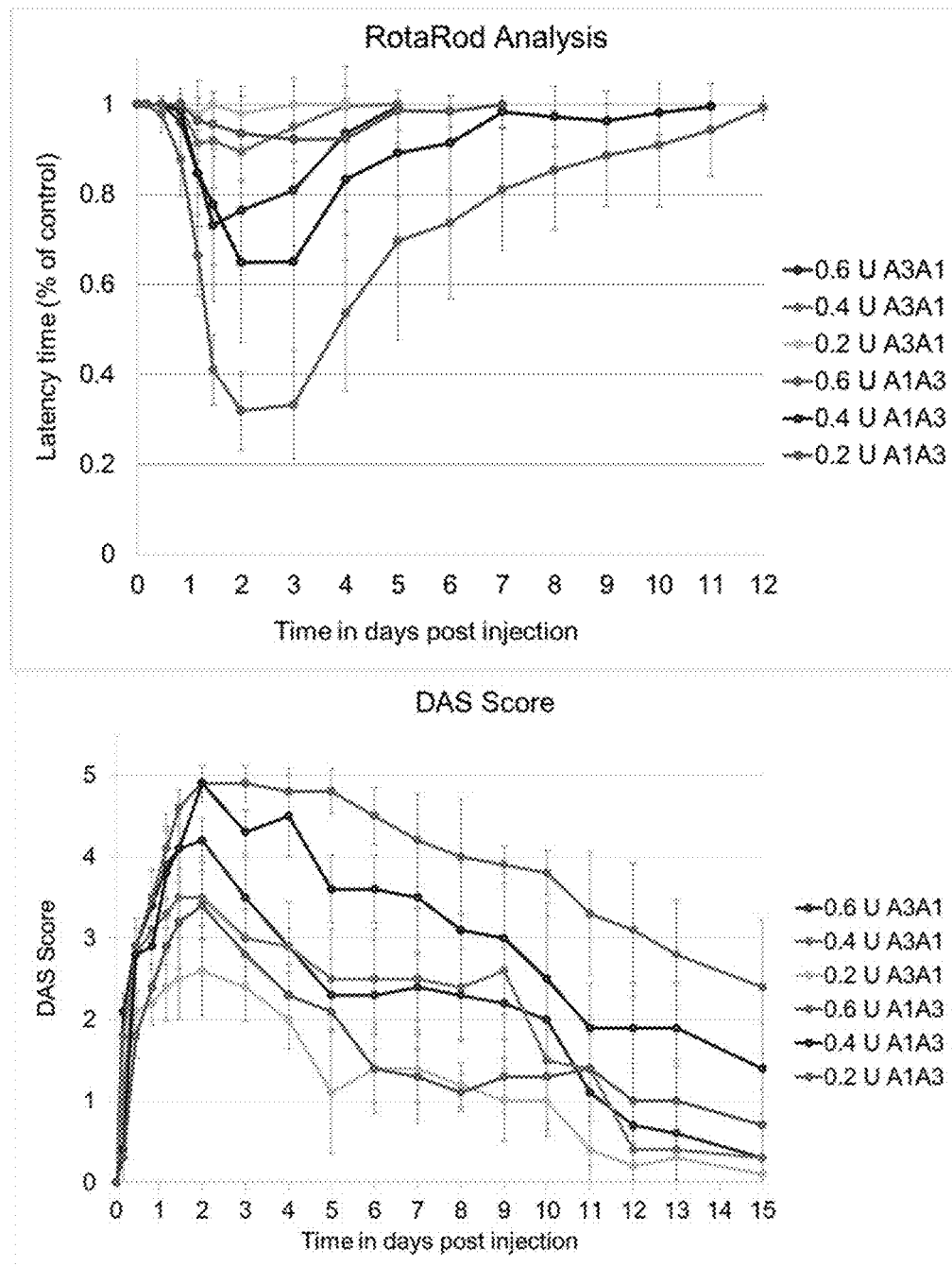

Data had indicated that the duration of action of BoNT/A3 in cultured neurons and in mice is significantly shorter than that of BoNT/A1. The duration of action of the hybrid toxins in cultured primary rat spinal cord neurons was determined as previously described by first exposing the neurons to the same amount of toxin and periodically determining SNAP-25 cleavage in cell sample over the next 10 months. The BoNT/A1A3 hybrid toxin resulted in very little gradual recovery in full-length SNAP-25 similar to what had previously been observed for BoNT/A1, while the BoNT/A3A1 hybrid resulted in almost immediately starting steady recovery that was almost complete after 5 months, similar as BoNT/A3 (FIG. 5B). Functional recovery from the hybrid toxins was examined in the mouse model as previously done for BoNT/A1 and /A3. After local injection of the toxins into the gastrocnemius muscle of the right hindlimb, local paralysis was assessed by DAS score and overall motorneurons deficiency of the animals by Rotarod analysis. Mice injected with BoNT/A1A3 recovered similar as had been previously observed for mice injected with BoNT/A1, whereas mice injected with BoNT/A3A1 recovered much faster and similar to previously observed data from mice injected with BoNT/A3 (FIG. 5C). These data demonstrate that the shorter duration of action of BoNT/A3 is solely determined by its LC domain.

BoNT/A3 LC has an Intracellular Localization Distinct from BoNT/A1 LC.

Figure 6:
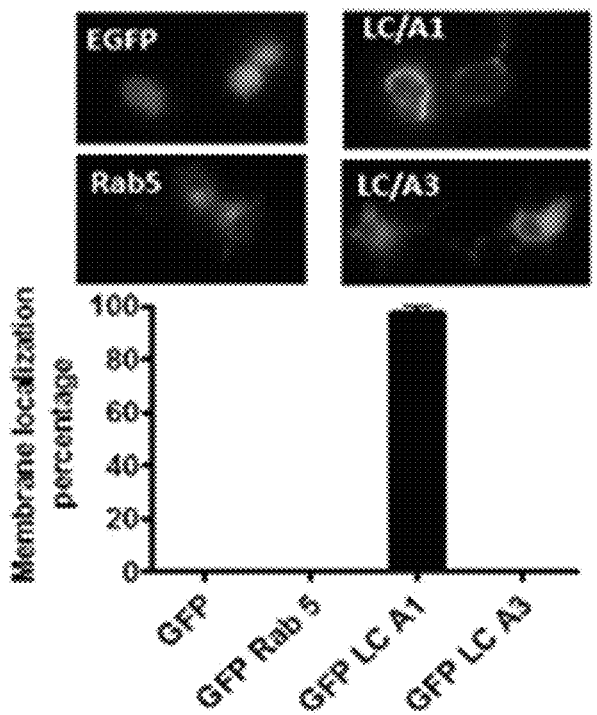
FIG. 6 shows the intracellular localization of BoNT/A1 and A3 LCs
Figure 7:
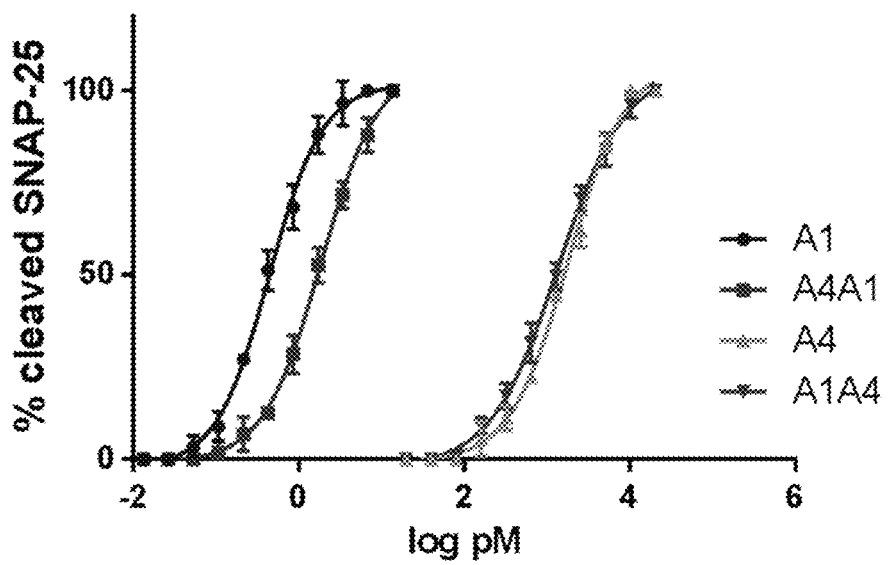
FIG. 7 shows the activity of BoNT/A1A4 and A4A1 subtype chimeras in human neurons.

The majority of previous data on intracellular localization of the long-lived BoNT/A1 and the short lived BoNT/E1 LC have indicated that BoNT/A1 LC localized to the plasma membrane of neuronal cell lines, whereas the BoNT/E1 LC localized to the cytoplasm (Fernandez-Salas et al., Mov Disord. 2004; 19 Suppl 8:S23-34. Epub 2004 Mar. 18; Fernandez-Salas et al., Proc Natl Acad Sci USA. 2004; 101(9):3208-13. Epub 2004 Feb. 26; Chen et al., J Biol Chem. 2011; 286(17):15067-72. Epub 2011 Mar. 8). In order to determine intracellular localization of the BoNT/A3 LC, BoNT/A1 LC-GFP or BoNT/A1 LC-GFP fusion proteins were expressed in neuro-2a cells. Immunofluorescence microscopy on these cells with counter-staining of the membranes using wheat germ agglutinin indicated that LC/A1-GFP but not LC/A3-GFP localized to the plasma membrane (FIG. 6). Instead, staining from the LC/A3-GFP was distributed throughout the cytosol with nuclear exclusion, similarly as has been previously described for BoNT/E1.

The Decreased Potency of BoNT/A4 is Primarily Determined by its HC Domain.

In experiments described herein, hybrid toxins combining the HC and LC domains of BoNT/A1 and A3 and were produced in a native clostridial expression host (FIG. 1), ensuring natural post-translation processing. Analysis of the hybrid toxins in cultured neurons and in mice indicated that the LC domain of the toxins is solely responsible for the duration of action (FIG. 5), while potency in human neurons is determined by both, the HC and LC domains of the toxins (FIG. 5A). This may be due to the differences in enzyme kinetics between the BoNT/A1 and A3 LC as well as to structural differences in the ganglioside binding pocket and receptor binding domain of the two toxins (Whitemarsh et al., Infect Immun. 2013; 81(10):3894-902. Epub 2013 Aug. 7; Henkel et al., Biochemistry. 2009; 48(11):2522), such that both the cell entry and the activity inside the cells cytosol is altered.

Figure 8A:
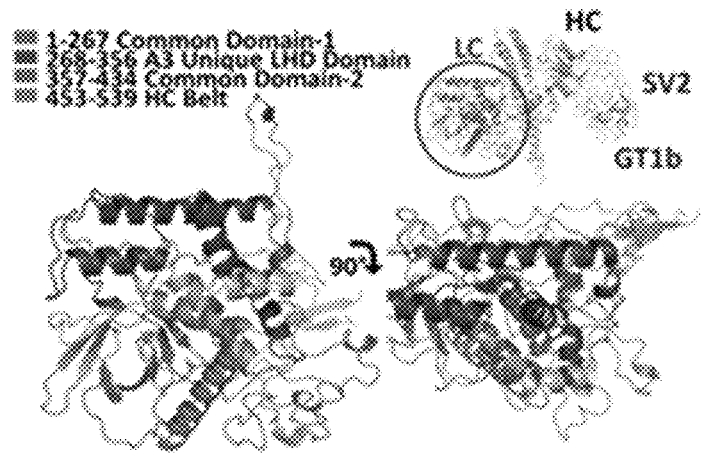
FIG. 8A-C shows structural modeling of critical domains of BoNT/A subtypes. Structural modeling was used to predict the molecular basis for the shorter duration of BoNT/A3 pathology (A), the molecular basis for the differential entry and pathology of BoNT/A1 and BoNT A2 (B), and the molecular mechanism underlying the reduced toxicity of BoNT/A4. (C).
Figure 8B:
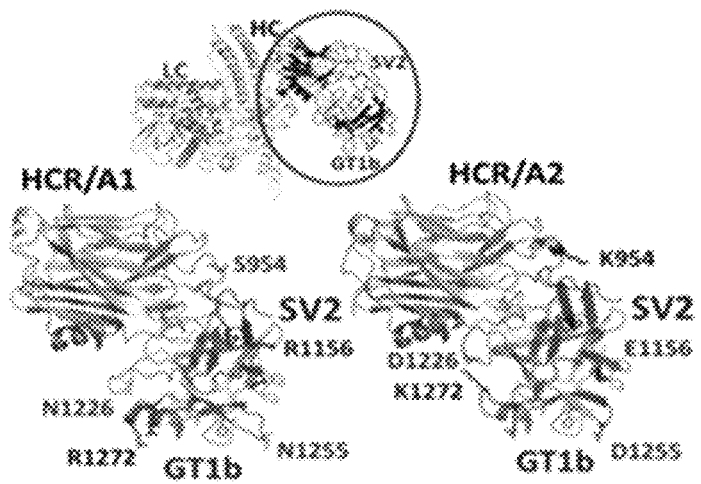
Figure 8C:
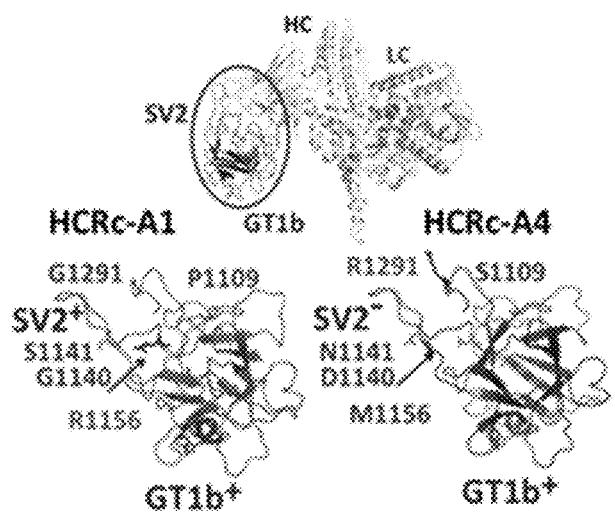

Expression of BoNT/A3 LC-GFP and BoNT/A1 LC-GFP fusion proteins in neuro-2a cells showed that the BoNT/A3 LC-GFP fusion protein distributed to the cytosol similarly as has been previously reported for the BoNT/E1 LC-GFP fusion protein, while the A1 LC-GFP fusion protein localized to the plasma membrane (FIG. 6). These data indicate that intracellular localization of the LC may play a role in determining its half-life inside neuronal cells. Structural modeling of the BoNT/A1 and A3 LCs revealed a previously unrecognized Localized region of High Dissimilarity (LHD) at residues 268-356, where LC/A3 shares only 55% primary amino acid identity with LC/A2 (FIG. 8 A).

Mice were shown to recover from paralysis and systemic symptoms after local BoNT injection significantly faster than humans (e.g. 2-4 weeks for BoNT/A1 compared to 3-6 months in humans for the same toxin). This was true for all toxin serotypes and indicates faster recovery in mice compared to humans. In this study, mice locally injected with the BoNT/A3A1 hybrid suffered little overall motorneuron deficiency as tested by Rotarod analysis (FIG. 5C), whereas local paralysis assessed by the DAS assay was significant, although as expected of shorter duration as that caused by BoNT/A1A3 (FIG. 5C). This is in agreement with the data derived from long-term activity in cultured neurons (FIG. 5A), where BoNT/A3 had some (slowly waning) activity remaining for 4-5 months. This is in contrast with BoNT/E1, which has been shown to lead to full recovery of intoxicated neurons after about one month (Keller et al., FEBS letters. 1999; 456(1):137-42; Whitemarsh et al., PLoS One. 2014; 9(2):e90252. Epub 2014 Mar. 4). Thus, it is unlikely that the intracellular localization alone determines the intracellular half-life of the various BoNT LCs and functional recovery.

The data indicate that faster cell entry kinetics by BoNT/A2 is due to the C-terminal portion of the HCR, and that lower potency of /A4 is localized to the HC. Only few amino acid residues differ in the C-terminal portion of the HCR of /A2 and /A1, and structural modeling indicates that the rapid entry and pathology elicited by BoNT/A2 is due to the organization of charged amino acids within the HCR adjacent to 1) the ganglioside-binding site (GT1b), increasing affinity for gangliosides and 2) the SV2-binding site (SV2), modulating entry into neurons (FIG. 8 B). Clustal Omega alignment of the five BoNT/A subtypes (A1-A5) revealed that only 10-amino acids are unique to BoNT/A4, and structural modeling of HCR/A4 on the crystal structure of HCR/A1 revealed a similar ganglioside binding site (GT1b site) but several unique amino acids within and adjacent to the SV2 binding site (SV2 site) (FIG. 8 C). This indicates that unique amino acids of HCR/A4 within (aa 1140 and 1141) and/or adjacent (aa 1156, 1291, 1109) to the SV2 binding site are responsible for the inability of HCR/A4 to enter synaptic vesicles in response to membrane depolarization (FIG. 8).

In summary, this Example presents data demonstrating functional subtype hybrid toxins of BoNTs engineered and expressed in either endogenous or *E. coli* expression systems without addition of linkers or tags (although linkers and tags may be employed, if desired). The expressed toxins are purified from the expression host and possess isotype-specific functional characteristics. Six specific exemplary hybrid toxins with unique pharmacologic characteristics have been described to illustrate the hybrids provided herein.

TABLE 2

Schematic presentation of recombinant hybrid serotype A BoNTs composed of combinations of subtype A1, A2, A3 and A4 Light (LC) and Heavy (HC) chains.

| | Native BoNT | Gene length bp | |
|---|---|---|---|
| | BoNT/A1 | 3891 bp | |
| | BoNT/A2 | 3891 bp | |
| | BoNT/A3 | 3879 bp | |
| | BoNT/A4 | 3891 bp | |
| Hybrid toxin | Composition | LC-gene portion in bp | HC-gene portion in bp |
| rA1 A2 | LC/A1-HC/A2 | 1-1332 bp of BoNT/A1 | 1333-3891 bp of BoNT/A2 |
| rA1 A3 | LC/A1-HC/A3 | 1-1332 bp of BoNT/A1 | 1321-3879 bp of BoNT/A3 |
| rA1 A4 | LC/A1-HC/A4 | 1-1332 bp of BoNT/A1 | 1333-3891 bp of BoNT/A4 |
| rA2 A1 | LC/A2-HC/A1 | 1-1332 bp of BoNT/A2 | 1333-3891 bp of BoNT/A1 |
| rA3 A1 | LC/A3-HC/A1 | 1-1320 bp of BoNT/A3 | 1333-3891 bp of BoNT/A1 |
| rA4 A1 | LC/A4-HC/A1 | 1-1332 bp of BoNT/A4 | 1333-3891 bp of BoNT/A1 |

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

We claim:

1. A hybrid botulinum neurotoxin (BoNT) toxin molecule comprising a light chain polypeptide from a first subtype and heavy chain polypeptide from a second subtype, wherein the hybrid is selected from the group consisting of A1/A2 A2/A1, A1/A3, A3/A1, A1/A4 and A4/A1.

2. The molecule of claim 1, wherein said molecule exhibits one or more properties selected from the group consisting of altered duration of action relative to BoNTs having light chains and heavy chains of the same subtype, altered neuronal selectivity relative to BoNTs having light chains and heavy chains of the same subtype, altered potency relative to BoNTs having light chains and heavy chains of the same subtype, altered onset of action relative to BoNTs having light chains and heavy chains of the same subtype, and altered uptake or transport relative to BoNTs having light chains and heavy chains of the same subtype.

3. The molecule of claim 1, wherein said molecule exhibits longer duration, higher potency, and altered neuronal distribution relative to BoNTs having light chains and heavy chains of the same subtype.

4. The molecule of claim 1, wherein said molecule exhibits longer duration, higher potency, and faster cell entry and intracellular transport relative to BoNTs having light chains and heavy chains of the same subtype.

5. The molecule of claim 1, wherein said molecule further comprises one or more amino acid changes that alter a property selected from the group consisting of duration, potency, and cell entry and intracellular transport speed.

6. The molecule of claim 1, wherein said molecule has a serotype selected from the group consisting of A, B, C1, D, E, F, and G.

7. The molecule of claim 6, wherein said light chain and said heavy chain have the same or different serotypes.

8. A composition comprising the molecule of claim 1.

9. The composition of claim 8, wherein said composition is a pharmaceutical composition.

10. The composition of claim 9, wherein said composition further comprises a pharmaceutically acceptable carrier.

11. A method, comprising: administering the molecule of claim 1 to a subject in need thereof.

12. The method of claim 11, wherein said administration is local or systemic.

\* \* \* \* \*